US009852504B2

(12) United States Patent
Begin et al.

(10) Patent No.: US 9,852,504 B2
(45) Date of Patent: Dec. 26, 2017

(54) AUTOMATIC STENT DETECTION

(71) Applicant: VOLCANO CORPORATION, San Diego, CA (US)

(72) Inventors: Elizabeth Begin, Billerica, MA (US); Nathaniel J. Kemp, Concord, MA (US); Jason Sproul, Watertown, MA (US); Badr Elmaanaoui, Billerica, MA (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

(21) Appl. No.: 15/094,577

(22) Filed: Apr. 8, 2016

(65) Prior Publication Data

US 2016/0292857 A1 Oct. 6, 2016

Related U.S. Application Data

(63) Continuation of application No. 14/044,441, filed on Oct. 2, 2013, now Pat. No. 9,307,926.
(Continued)

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0066* (2013.01); *A61B 5/0073* (2013.01);
(Continued)

(58) Field of Classification Search
CPC ... A61B 5/0066; A61B 5/0073; A61B 8/0841; A61B 8/5223; A61B 8/5261;
(Continued)

(56) References Cited

U.S. PATENT DOCUMENTS

| 8,025,622 B2* | 9/2011 | Rold | A61B 8/12 600/437 |
|---|---|---|---|
| 2002/0049375 A1* | 4/2002 | Strommer | A61B 5/0066 600/407 |

(Continued)

OTHER PUBLICATIONS

Sung, Kah-Kay et al "Example-based Learning for View-based Human Face Detection", Artificial Intelligence Laboratory, Image Understanding Workshop, vol. 2, Nov. 1994, pp. 843-850.
(Continued)

*Primary Examiner* — Tom Y Lu

(57) ABSTRACT

This invention relates generally to the detection of objects, such as stents, within intraluminal images using principal component analysis and/or regional covariance descriptors. In certain aspects, a training set of pre-defined intraluminal images known to contain an object is generated. The principal components of the training set can be calculated in order to form an object space. An unknown input intraluminal image can be obtained and projected onto the object space. From the projection, the object can be detected within the input intraluminal image. In another embodiment, a covariance matrix is formed for each pre-defined intraluminal image known to contain an object. An unknown input intraluminal image is obtained and a covariance matrix is computed for the input intraluminal image. The covariances of the input image and each image of the training set are compared in order to detect the presence of the object within the input intraluminal image.

19 Claims, 17 Drawing Sheets

Related U.S. Application Data

(60) Provisional application No. 61/710,429, filed on Oct. 5, 2012.

(51) Int. Cl.

| | | |
|---|---|---|
| *A61B 5/06* | (2006.01) | |
| *A61B 5/00* | (2006.01) | |
| *A61B 8/08* | (2006.01) | |
| *A61B 8/12* | (2006.01) | |
| *G06K 9/62* | (2006.01) | |
| *A61B 34/20* | (2016.01) | |
| *G06T 7/70* | (2017.01) | |
| *G06T 7/73* | (2017.01) | |
| *A61B 8/14* | (2006.01) | |
| *A61B 8/00* | (2006.01) | |

(52) U.S. Cl.
CPC ............ *A61B 5/061* (2013.01); *A61B 5/6852* (2013.01); *A61B 8/0841* (2013.01); *A61B 8/12* (2013.01); *A61B 8/5223* (2013.01); *A61B 8/5261* (2013.01); *A61B 34/20* (2016.02); *G06K 9/6247* (2013.01); *G06K 9/6274* (2013.01); *G06T 7/0014* (2013.01); *G06T 7/70* (2017.01); *G06T 7/74* (2017.01); *A61B 8/14* (2013.01); *A61B 8/4416* (2013.01); *G06T 2207/10072* (2013.01); *G06T 2207/10081* (2013.01); *G06T 2207/10101* (2013.01); *G06T 2207/10132* (2013.01); *G06T 2207/10136* (2013.01); *G06T 2207/20048* (2013.01); *G06T 2207/20076* (2013.01); *G06T 2207/20081* (2013.01); *G06T 2207/30021* (2013.01); *G06T 2207/30101* (2013.01)

(58) Field of Classification Search
CPC ........ G06K 9/6247; G06T 2207/10072; G06T 2207/10136; G06T 2207/20048; G06T 2207/20081; G06T 2207/301
See application file for complete search history.

(56) References Cited

U.S. PATENT DOCUMENTS

| | | | |
|---|---|---|---|
| 2006/0187462 A1* | 8/2006 | Srinivasan | A61B 3/102 356/479 |
| 2009/0018393 A1* | 1/2009 | Dick | A61B 5/0062 600/109 |
| 2012/0075638 A1* | 3/2012 | Rollins | A61B 1/00009 356/479 |

OTHER PUBLICATIONS

Osuna, Edgar et al "Training Support Vector Machines: An Application to Face Detection", Computer Vision and Pattern Recognition, Jun. 1997, pp. 130-136.

Kompatsiaris, Ioannis et al "Deformable Boundary Detection of Stents in Angiographic Images", IEEE Transactions on Medical Imaging, vol. 19, No. 6, Jun. 2000.

Kilic, Niyazi et al "Classification of the Colonic Polyps in CT-Colonography using Region Covariance as Descriptor Feastures of Suspicious Regions", Journal of Medical Systems , vol. 34, No. 2, Oct. 2008, pp. 101-105.

* cited by examiner

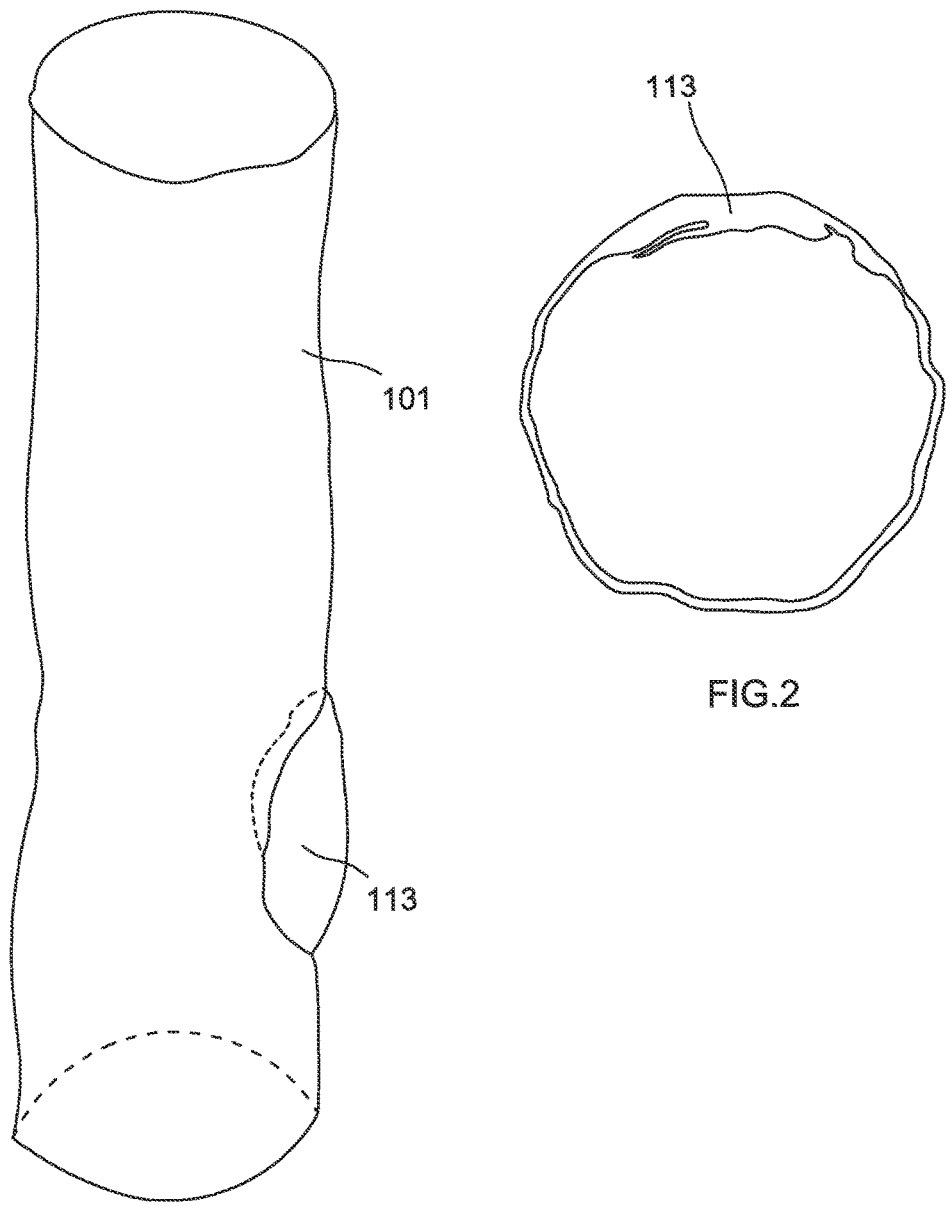

AUTOMATIC STENT DETECTION

RELATED APPLICATION

This application is a continuation of U.S. Non-Provisional application Ser. No. 14/044,441, filed Oct. 2, 2013, now U.S. Pat. No. 9,307,926, which claims the benefit of and priority to U.S. Provisional No. 61/710,429, filed Oct. 5, 2012, both of which are incorporated by reference in their entirety.

TECHNICAL FIELD

This invention generally relates to the automatic detection of stents in intraluminal imaging.

BACKGROUND

Tomographic imaging is a signal acquisition and processing technology that allows for high-resolution cross-sectional imaging in biological systems. Tomographic imaging systems include, for example, optical coherence tomography systems, ultrasound imaging systems, and computed tomography. Tomographic imaging is particularly well-suited for imaging the subsurface of a vessel or lumen within the body, such as a blood vessel, using probes disposed within a catheter through a minimally invasive procedure.

Typical tomographic imaging catheters consist of an imaging core that rotates and moves longitudinally through a blood vessel, while recording an image video loop of the vessel. The motion results in a 3D dataset, where each frame provides a 360 degree slice of the vessel at different longitudinal section. These frames provide cardiologists with invaluable information such as the location and severity of the stenosis in a patient, the presence of vulnerable plagues, and changes in the disease over time. The information also assists in determining the appropriate treatment plan for the patient, such as drug therapy, stent placement, angioplasty, or bypass surgery.

One of the most common analyses performed is the placement and apposition of stents. A stent is a small, typically meshed or slotted, tube-like structure made of a metal or polymer that is inserted into the blood vessel to hold vessel open and keep it from occluding and provides a framework for arterial lesions that are likely to embolize after balloon angioplasty. During placement, the stent should be placed in parallel within the vessel and contact the vessel wall. Apposition of a coronary artery stent is the term for how well stent lies against the wall of the artery. When the stent as placed does not mesh completely against the blood vessel, the stent is in 'incomplete apposition'. Incomplete apposition may raise the risk of a subsequent blockage or thrombus because of blood pooling or stagnating in the dead space between the stent and the coronary artery wall. Therefore, it is critical to verify that the stent is properly employed.

In order to identify and measure stent opposition in intravascular images, a cardiologist typically has to manually locate the stent struts, which are the framework of the stent visible in the tomographic image. Generally, identification of at least two stent struts is required to determine stent apposition. This process can be a very time consuming and is prone to user error.

SUMMARY

This invention generally improves the ability of user of a tomographic imaging system to quickly assess a deployed stent by providing a method for detecting the stent location. Through use of the image processing techniques, the stent locations for all frames or a subset of frames in a recorded dataset for an imaging run are detected and provided to the user. The resulting stent detections may be displayed on the tomographic image, the image longitudinal display (ILD) or displayed on 3-D reconstructions of the vessel. This advantageously eliminates the need for the user to manually locate the stent struts in order to quantify the apposition. Moreover, automatically detecting stents reduces error associated with manual detection and provides a more reliable means to detect and remedy mal-apposed stents.

Tomographic imaging systems suitable for use in aspects of the invention include any tomographic cross-sectional imaging system capable of obtaining intraluminal images, such as optical coherence tomography systems, ultrasound imaging systems and combined OCT-ultrasound imaging systems. Intraluminal images are typically intravascular images, but also include any image taken within a biological lumen, such as an intestinal lumen.

This invention relates to computing systems and methods for computer-assisted detection of a stent, a stent strut, or a portion of the stent, and can also be used to detect other objects within intraluminal images such as tissue or a guidewire. Objects are identified based on the locations in the polar coordinate system using data obtained from one-dimensional, two dimensional or three-dimensional images. Once stent struts are identified, measurements of the stent apposition or coverage relative to the lumen border can be easily computed.

In one aspect, a set of pre-defined intraluminal images that are known to display a object are generated to train a processor to identify or recognize the object in intraluminal images unknown to contain the object, for example, input intraluminal images of a patient undergoing an OCT examination. For example, in this step, a set of pre-defined intraluminal data images can include a plurality of intraluminal images known to display a stent strut so that a processor can be trained to identify the stent strut. After a training set of the pre-defined intraluminal images is generated, the principal components for the set can be computed to create an object space for the object. The principal components for the object can be stored and used to detect the object in input intraluminal images that are unknown to contain the object. By projecting the input intraluminal image onto the object space, the object can be detected within the input intraluminal image.

In certain embodiments, after the input intraluminal image is projected onto the object space, the error, for example, the Euclidean distance, between the input intraluminal image and the object space image is determined. A small error can constitute a positive detection of the object within input intraluminal image. The image can then be post-processed to identify or highlight the detected object within the input intraluminal image. Post-processing can also include removing false object detections from the input intraluminal image.

In some embodiments, at least two sets of pre-defined intraluminal images known to display different objects are generated, for example, a set of pre-defined intraluminal images known to display stents and a set of pre-defined intraluminal images known to display tissue. The principal components for each set can be computed to generate an object space for each object. An input intraluminal image unknown to display either object is projected onto each object space and the objects are detected within the input intraluminal images. The objects can be detected by calculating an error between the input intraluminal image and each object space. The object space that most accurately represents the input intraluminal image, for example, has the smallest error, is indicative of a positive detection of the corresponding object to the object space. The object space with the larger error can be indicative of a negative detection for its corresponding object. This advantageously increases the accuracy of the detection because instead of detecting based on error alone, detection is based on the combination of error and a comparison of the errors.

In another aspect, an object, such as stent, can be detected within an input intraluminal image by generating a training set of intraluminal images of an object, where each image is defined by one or more features. A covariance matrix can be computed for a feature within each pre-defined intraluminal image of the training set. The covariance for a feature within the input intraluminal image can be calculated and compared to the covariances of the training set. From the comparison, the object can be detected within the input intraluminal image. In certain aspects, the feature can be the Cartesian coordinates of a pixel, the intensity at each pixel, or the first and second order derivatives of the image in the x and y direction.

Other and further aspects and features of the invention will be evident from the following detailed description and accompanying drawings, which are intended to illustrate, not limit, the invention.

BRIEF DESCRIPTION OF DRAWINGS

FIG. 1 is a perspective view of a vessel.

FIG. 2 is a cross sectional view of the vessel shown in FIG. 1.

DESCRIPTION

Figure 3:
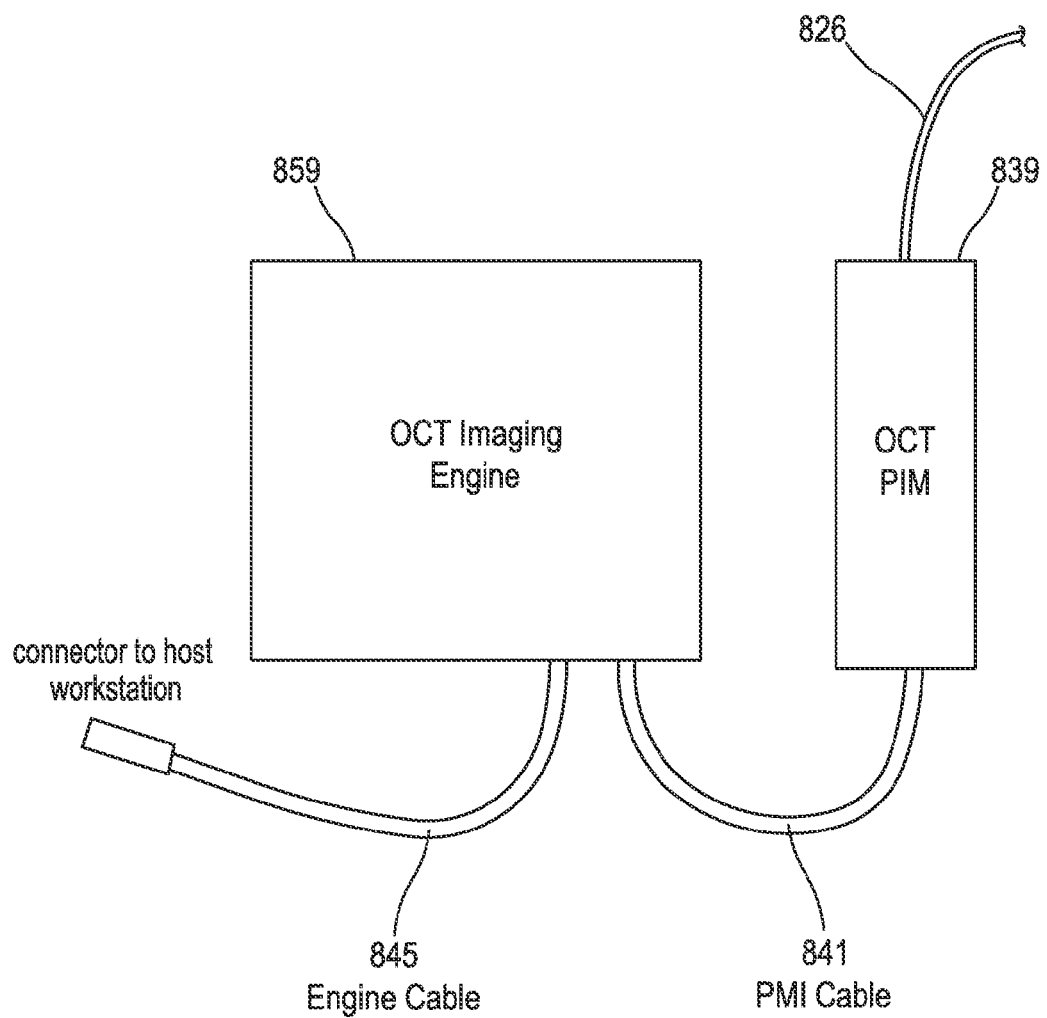
FIG. 3 is a diagram of components of an optical coherence tomography (OCT) system.

This invention generally relates to automatically detecting stents in intraluminal medical imaging. Medical imaging is a general technology class in which sectional and multidimensional anatomic images are constructed from acquired data. The data can be collected from a variety of signal acquisition systems including, but not limited to, magnetic resonance imaging (MRI), radiography methods including fluoroscopy, x-ray tomography, computed axial tomography and computed tomography, nuclear medicine techniques such as scintigraphy, positron emission tomography and single photon emission computed tomography, photo acoustic imaging ultrasound devices and methods including, but not limited to, intravascular ultrasound spectroscopy (IVUS), ultrasound modulated optical tomography, ultrasound transmission tomography, other tomographic techniques such as electrical capacitance, magnetic induction, functional MRI, optical projection and thermo-acoustic imaging, combinations thereof and combinations with other medical techniques that produce one-, two- and three-dimensional images. Although the exemplifications described herein are drawn to the invention as applied to OCT, at least all of these techniques are contemplated for use with the systems and methods of the present invention.

Systems and methods of the invention have application in intravascular imaging methodologies such as intravascular ultrasound (IVUS) and optical coherence tomography (OCT) among others that produce a three-dimensional image of a lumen. A segment of a lumen 101 is shown in FIG. 1 having a feature 113 of interest. FIG. 2 shows a cross-section of lumen 101 through feature 113. In certain embodiments, intravascular imaging involves positioning an imaging device near feature 113 and collecting data representing a three-dimensional image.

OCT is a medical imaging methodology using a specially designed catheter with a miniaturized near infrared light-emitting probe attached to the distal end of the catheter. As an optical signal acquisition and processing method, it captures micrometer-resolution, three-dimensional images from within optical scattering media (e.g., biological tissue). Commercially available OCT systems are employed in diverse applications, including art conservation and diagnostic medicine, notably in ophthalmology where it can be used to obtain detailed images from within the retina. The detailed images of the retina allow one to identify several eye diseases and eye trauma. Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

Other applications of OCT and other signal processing imaging systems for biomedical imaging include use in: dermatology in order to image subsurface structural and blood flow formation; dentistry in order to image the structure of teeth and gum line to identify and track de-mineralization and re-mineralization, tarter, caries, and periodontal disease; gastroenterology in order to image the gastrointestinal tract to detect polyps and inflammation, such as that caused by Crohn's disease and ulcerative colitis; cancer diagnostics in order to discriminate between malignant and normal tissue.

Generally, an OCT system comprises three components which are 1) an imaging catheter 2) OCT imaging hardware, 3) host application software. When utilized, the components are capable of obtaining OCT data, processing OCT data, and transmitting captured data to a host system. OCT systems and methods are generally described in Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety. In certain embodiments, systems and methods of the invention include processing hardware configured to interact with more than one different three dimensional imaging system so that the tissue imaging devices and methods described here in can be alternatively used with OCT, IVUS, or other hardware.

Various lumen of biological structures may be imaged with aforementioned imaging technologies in addition to blood vessels, including, but not limited, to vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

The arteries of the heart are particularly useful to examine with imaging devices such as OCT. OCT imaging of the coronary arteries can determine the amount of plaque built up at any particular point in the coronary artery. The accumulation of plaque within the artery wall over decades is the setup for vulnerable plaque which, in turn, leads to heart attack and stenosis (narrowing) of the artery. OCT is useful in determining both plaque volume within the wall of the artery and/or the degree of stenosis of the artery lumen. It can be especially useful in situations in which angiographic imaging is considered unreliable, such as for the lumen of ostial lesions or where angiographic images do not visualize lumen segments adequately. Example regions include those with multiple overlapping arterial segments. It is also used to assess the effects of treatments of stenosis such as with hydraulic angioplasty expansion of the artery, with or without stents, and the results of medical therapy over time. In an exemplary embodiment, the invention provides a system for capturing a three dimensional image by OCT.

In OCT, a light source delivers a beam of light to an imaging device to image target tissue. Light sources can be broad spectrum light sources, pulsating light sources, continuous wave light sources, and include superluminescent diodes, ultrashort pulsed lasers and supercontinuum. Within the light source is an optical amplifier and a tunable filter that allows a user to select a wavelength of light to be amplified. Wavelengths commonly used in medical applications include near-infrared light, for example between about 800 nm and about 1700 nm.

Methods of the invention apply to image data obtained from obtained from any OCT system, including OCT systems that operate in either the time domain or frequency (high definition) domain. Basic differences between time-domain OCT and frequency-domain OCT is that in time-domain OCT, the scanning mechanism is a movable mirror, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference mirror, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images.

In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously. Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in its entirety.

In certain embodiments, the invention provides a differential beam path OCT system with intravascular imaging capability as illustrated in FIG. 3. For intravascular imaging, a light beam is delivered to the vessel lumen via a fiber-optic based imaging catheter 826. The imaging catheter is connected through hardware to software on a host workstation. The hardware includes an imagining engine 859 and a handheld patient interface module (PIM) 839 that includes user controls. The proximal end of the imaging catheter is connected to PIM 839, which is connected to an imaging engine as shown in FIG. 3.

Figure 4:
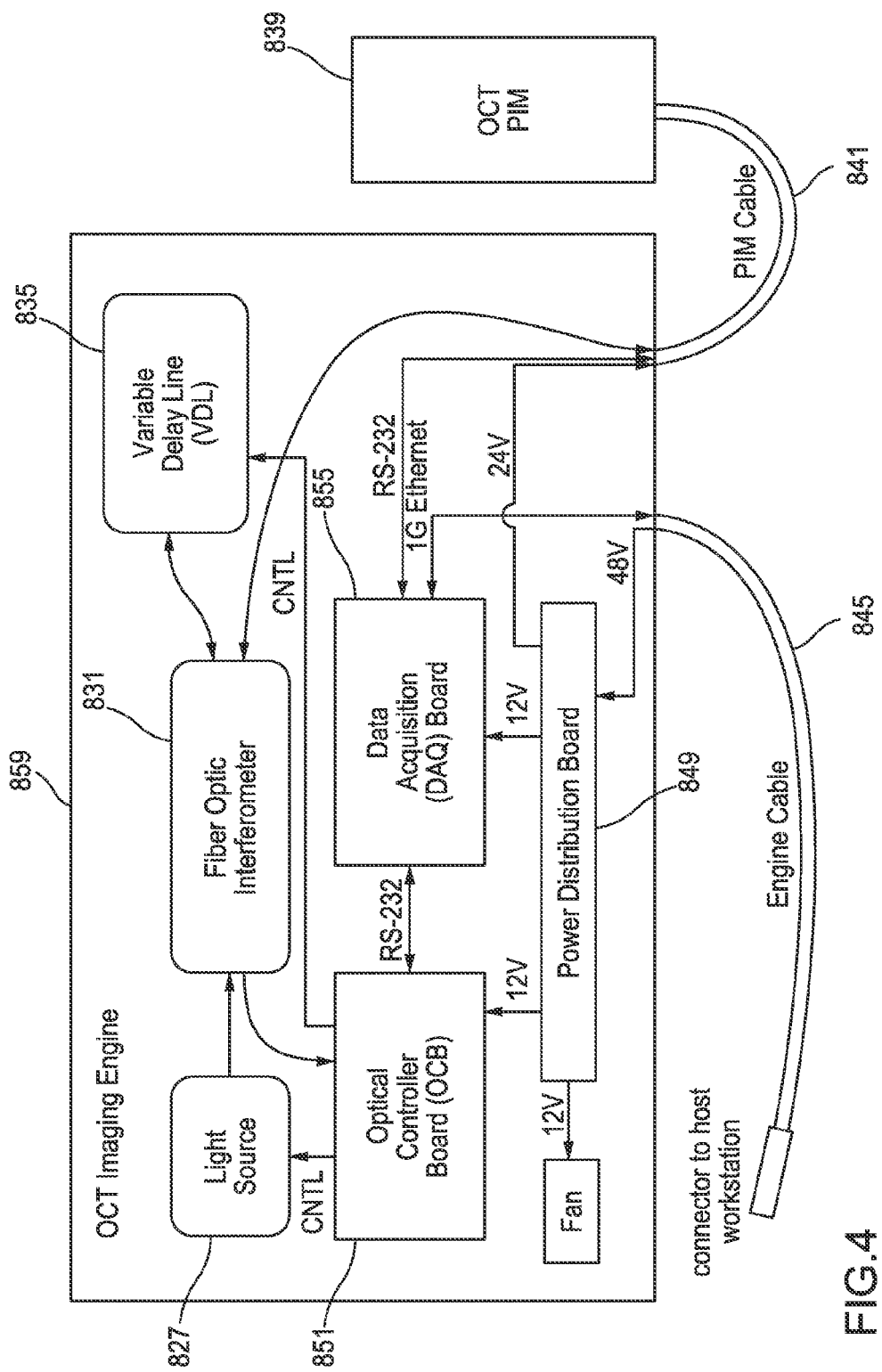
FIG. 4 is a diagram of the imaging engine shown in FIG. 3.

As shown in FIG. 4, the imaging engine 859 (e.g., a bedside unit) houses a power supply 849, light source 827, interferometer 831, and variable delay line 835 as well as a data acquisition (DAQ) board 855 and optical controller board (OCB) 851. A PIM cable 841 connects the imagine engine 859 to the PIM 839 and an engine cable 845 connects the imaging engine 859 to the host workstation.

Figure 5:
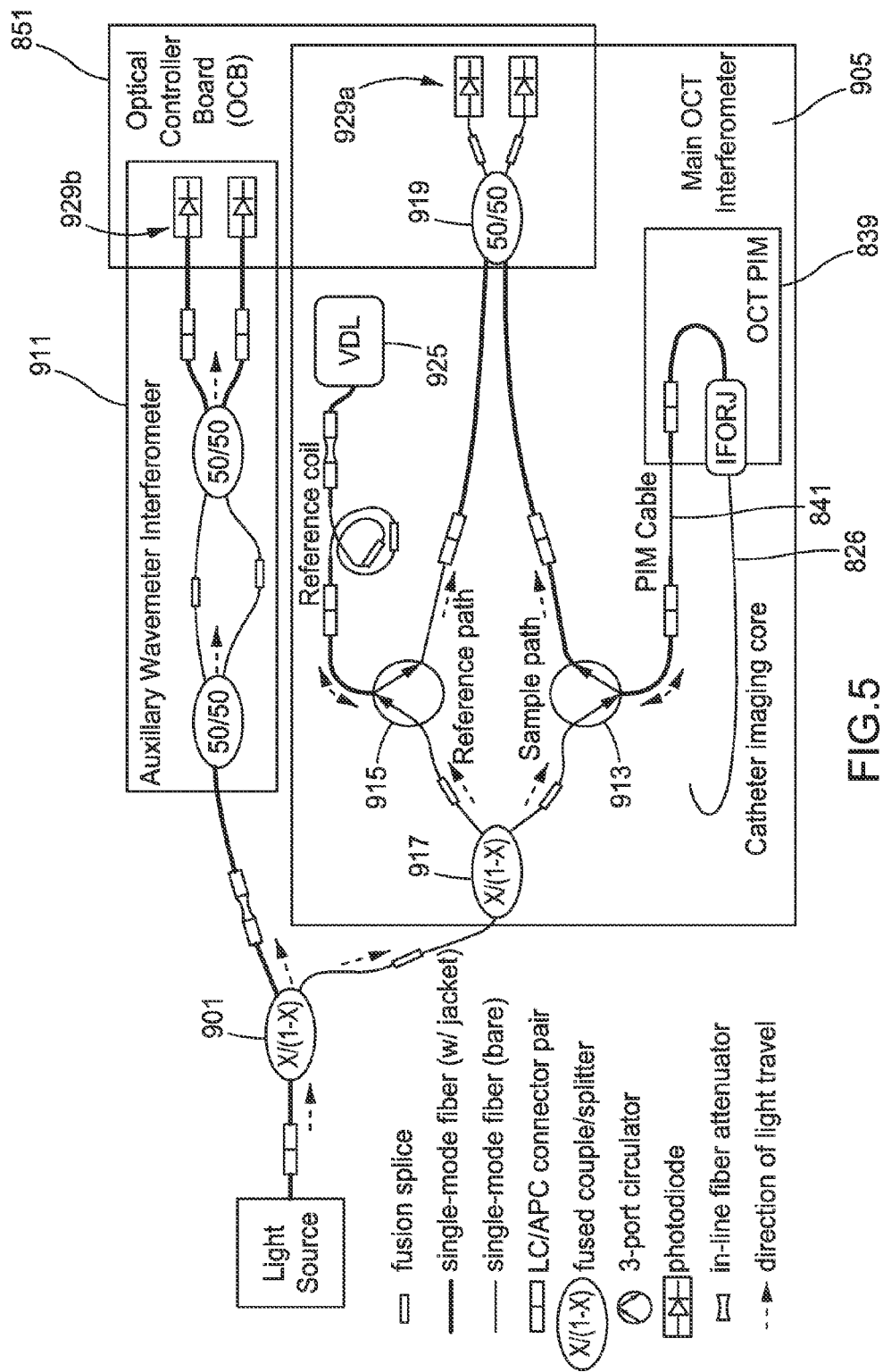
FIG. 5 is a diagram of a light path in an OCT system of certain embodiments of the invention.

FIG. 5 shows light path in a differential beam path system according to an exemplary embodiment of the invention. Light for image capture originates within the light source 827. This light is split between an OCT interferometer 905 and an auxiliary, or "clock", interferometer 911. Light directed to the OCT interferometer is further split by splitter 917 and recombined by splitter 919 with an asymmetric split ratio. The majority of the light is guided into the sample path 913 and the remainder into a reference path 915. The sample path includes optical fibers running through the PIM 839 and the imaging catheter 826 and terminating at the distal end of the imaging catheter where the image is captured.

Typical intravascular OCT involves introducing the imaging catheter into a patient's target vessel using standard interventional techniques and tools such as a guide wire, guide catheter, and angiography system. The imaging catheter may be integrated with IVUS by an OCT-IVUS system for concurrent imaging, as described in, for example, Castella et al. U.S. Patent Application Publication No. 2009/0043191 and Dick et al. U.S. Patent Application Publication No. 2009/0018393, both incorporated by reference in their entirety herein.

Figure 6:
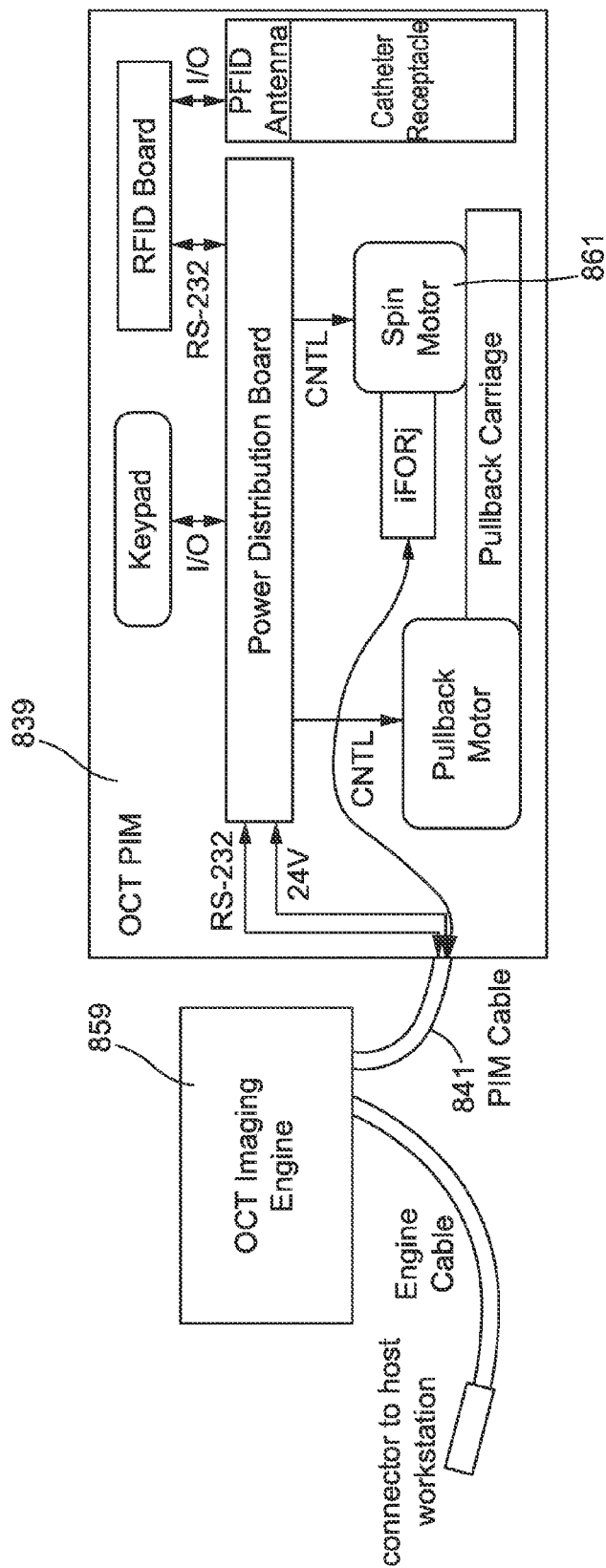
FIG. 6 is a patient interface module of an OCT system.
Figure 7:
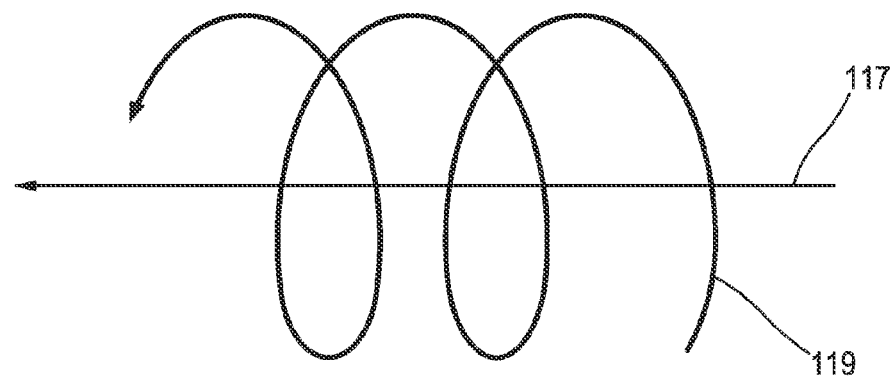
FIG. 7 is an illustration of the motion of parts of an imaging catheter according to certain embodiments of the invention.
Figure 8:
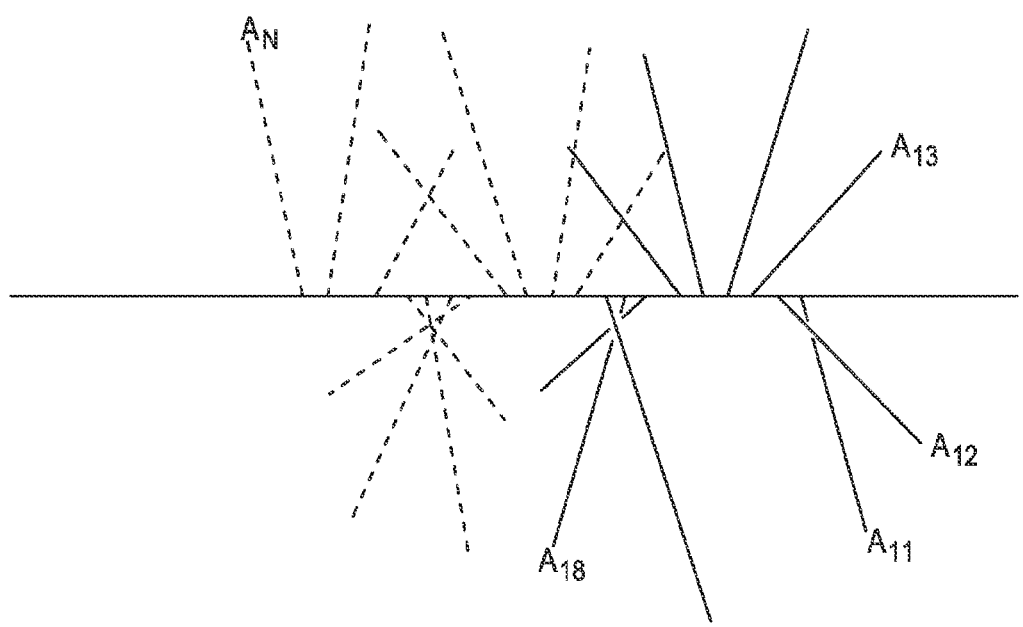
FIG. 8 shows an array of A scan lines of a three-dimensional imaging system according to certain embodiments of the invention.

Rotation of the imaging catheter is driven by spin motor 861 while translation is driven by pullback motor 865, shown in FIG. 6. This results in a motion for image capture described by FIG. 7. Blood in the vessel is temporarily flushed with a clear solution for imaging. When operation is triggered from the PIM or control console, the imaging core of the catheter rotates while collecting image data. Using light provided by the imaging engine, the inner core sends light into the tissue in an array of A-scan lines as illustrated in FIG. 8 and detects reflected light.

Figure 9:
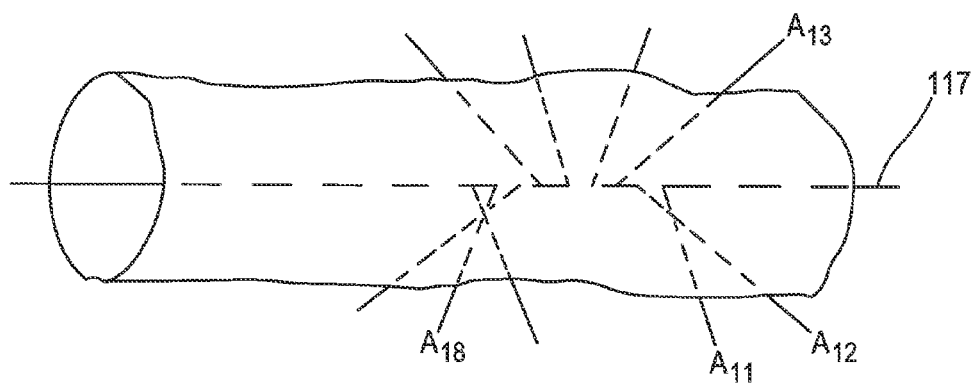
FIG. 9 shows the positioning of A scans with in a vessel.

FIG. 9 shows the positioning of A-scans within a vessel. Each place where one of A-scans A11, A12, . . . , AN intersects a surface of a feature within vessel 101 (e.g., a vessel wall) coherent light is reflected and detected. Catheter 826 translates along axis 117 being pushed or pulled by pullback motor 865.

The reflected, detected light is transmitted along sample path 913 to be recombined with the light from reference path 915 at splitter 919 (FIG. 5). A variable delay line (VDL) 925 on the reference path uses an adjustable fiber coil to match the length of reference path 915 to the length of sample path 913. The reference path length is adjusted by a stepper motor translating a mirror on a translation stage under the control of firmware or software. The free-space optical beam on the inside of the VDL 925 experiences more delay as the mirror moves away from the fixed input/output fiber.

The combined light from splitter 919 is split into orthogonal polarization states, resulting in RF-band polarization-diverse temporal interference fringe signals. The interference fringe signals are converted to photocurrents using PIN photodiodes 929a, 929b, . . . on the OCB 851 as shown in FIG. 5. The interfering, polarization splitting, and detection steps are done by a polarization diversity module (PDM) on the OCB. Signal from the OCB is sent to the DAQ 855, shown in FIG. 4. The DAQ includes a digital signal processing (DSP) microprocessor and a field programmable gate array (FPGA) to digitize signals and communicate with the host workstation and the PIM. The FPGA converts raw optical interference signals into meaningful OCT images. The DAQ also compresses data as necessary to reduce image transfer bandwidth to 1 Gbps (e.g., compressing frames with a glossy compression JPEG encoder).

Data is collected from A-scans A11, A12, . . . , AN and stored in a tangible, non-transitory memory. Typically, rotational systems consist of an imaging core which rotates and pulls back (or pushes forward) while recording an image video loop. This motion results in a three dimensional dataset of two dimensional image frames, where each frame provides a 360° slice of the vessel at different longitudinal locations.

Figure 10:
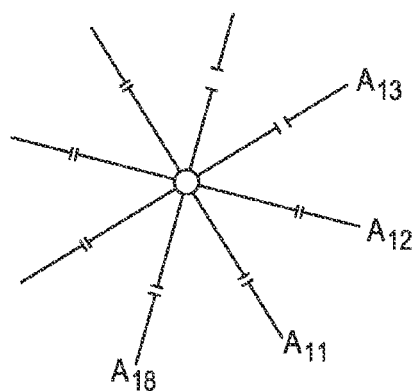
FIG. 10 illustrates a set of A scans used to compose a B scan according to certain embodiments of the invention.

A set of A-scans generally corresponding to one rotation of catheter 826 around axis 117 collectively define a B-scan. FIG. 10 illustrates a set of A-scans A11, A12, . . . , A18 used to compose a B-scan according to certain embodiments of the invention. These A-scan lines are shown as would be seen looking down axis 117 (i.e., longitudinal distance between then is not shown). While eight A-scan lines are illustrated in FIG. 10, typical OCT applications can include between 300 and 1,000 A-scan lines to create a B-scan (e.g., about 660). Reflections detected along each A-scan line are associated with features within the imaged tissue. Reflected light from each A-scan is combined with corresponding light that was split and sent through reference path 915 and VDL 925 and interference between these two light paths as they are recombined indicates features in the tissue.

Figure 11:
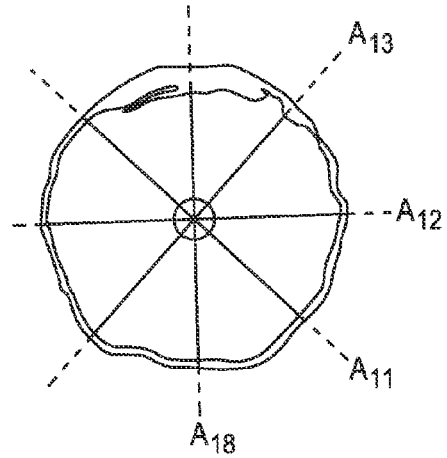
FIG. 11 shows the set of A scans shown in FIG. 10 within a cross section of a vessel.
Figure 12:
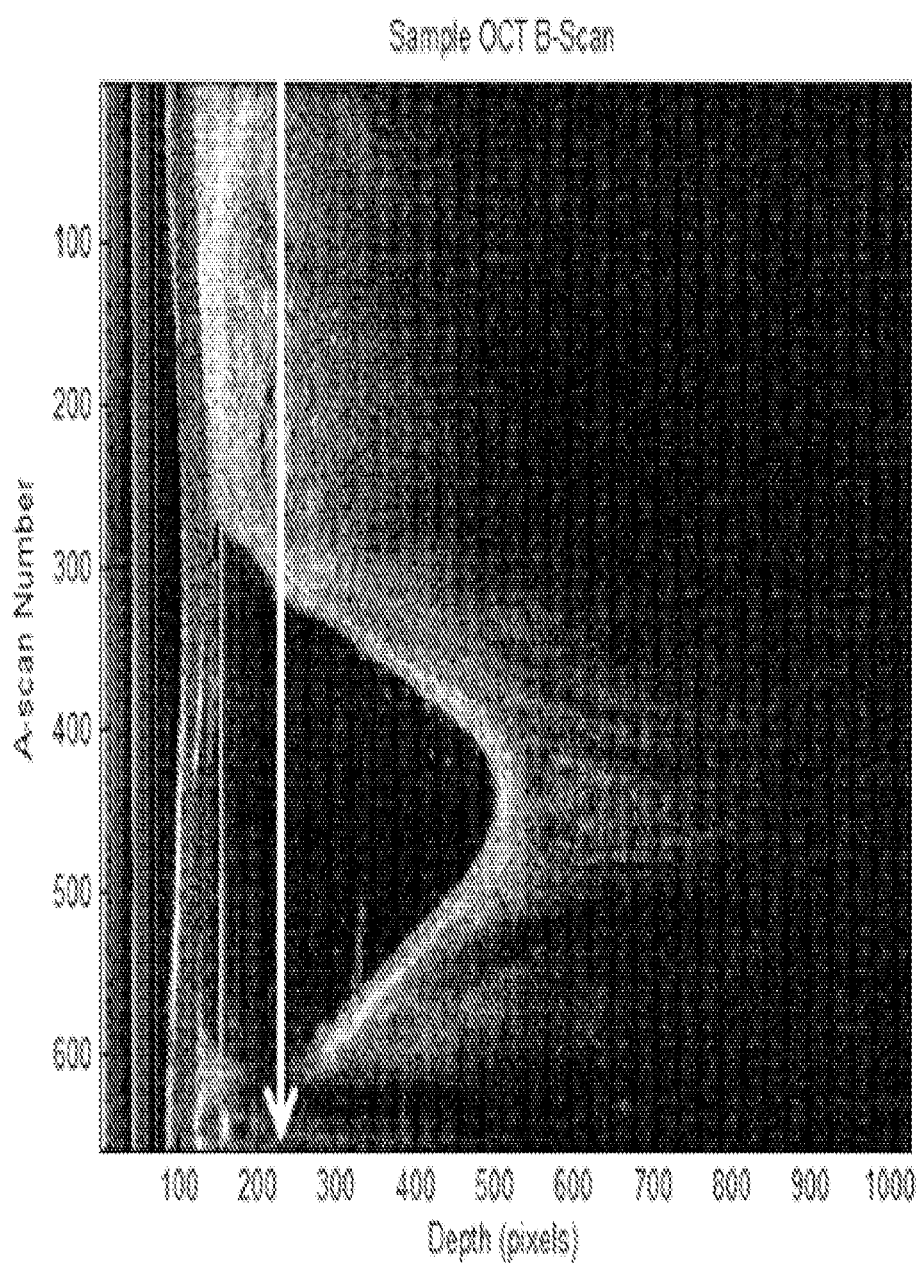
FIG. 12 shows a sample OCT B-Scan image calculated from 660 A-scans.
Figure 13:
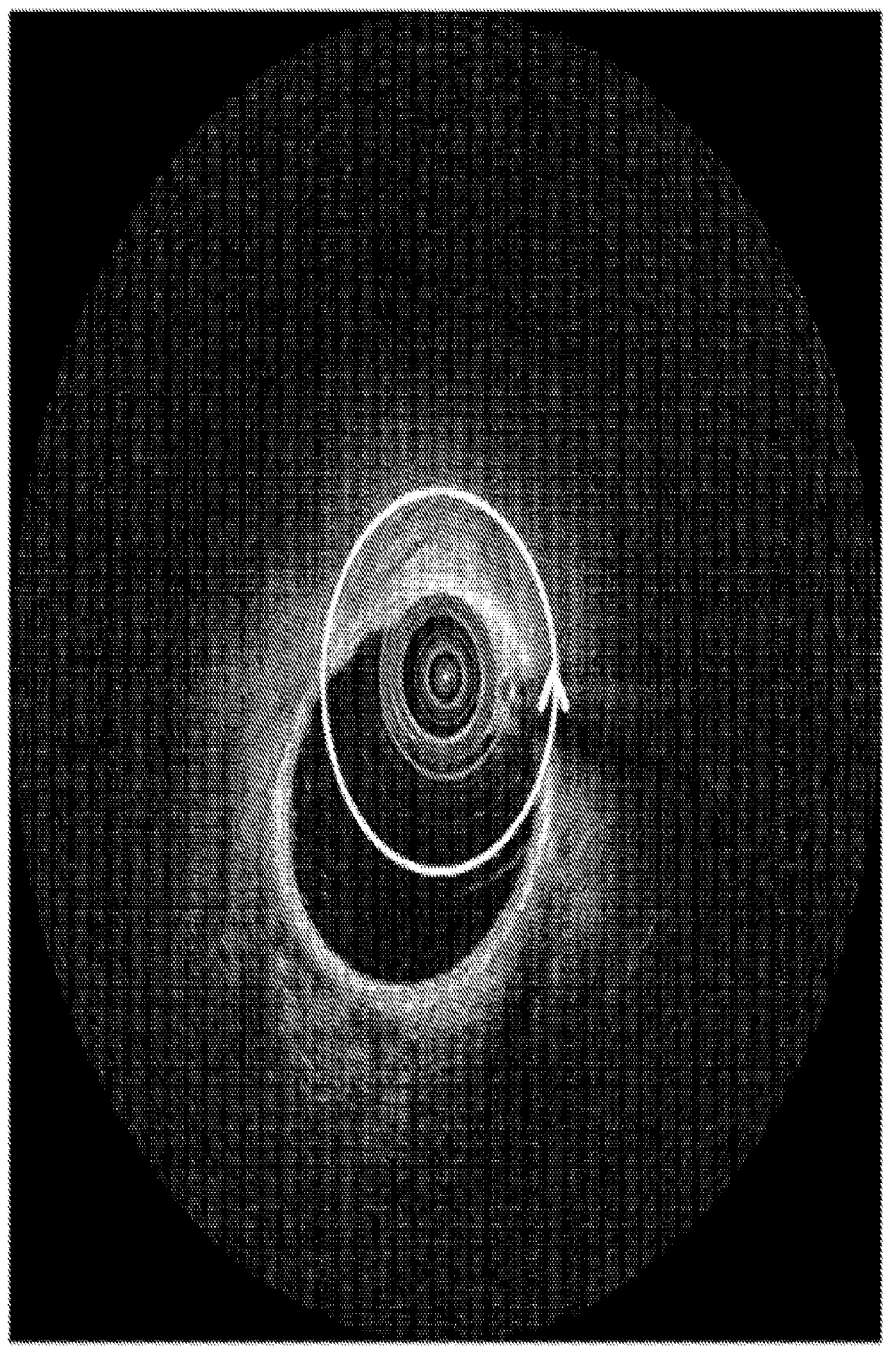
FIG. 13 shows a scan-converted OCT image from the B-scan of FIG. 12.

The data of all the A-scan lines together represent a three-dimensional image of the tissue. The data of the A-scan lines generally referred to as a B-scan can be used to create an image of a cross section of the tissue, sometimes referred to as a tomographic view. For example, FIG. 11 shows the set of A-scans shown in FIG. 10 within a cross section of a vessel. The set of A-scans obtained by rotational imaging modality can be combined to form a B-scan. FIG. 12 is an example of an OCT polar coordinate B-Scan with 660 A-scans. To create a final tomographic view of the vessel, the B-scan is scan converted to a Cartesian coordinate system. FIG. 13 displays the scan-converted image of the B-scan in FIG. 12.

Systems and methods of the invention include image-processing techniques that provide automatic detection of objects, such as stents, within intraluminal images. Typically, the OCT intraluminal image is an intravascular image taken within a lumen of a blood vessel, but the detection methods described herein can be used to detect objects within other biological lumens, such as the intestine. Although the following description is directed towards detecting objects in OCT images, one skilled in the art would readily recognize that methods and systems of intention can be utilized to detect objects in any intraluminal images obtained from any other imaging technique, such as intravascular ultrasound imaging (IVUS) and combined OCT-IVUS.

Embodiments of the invention provide for algorithms to detect a stents location within the polar coordinate system using features within one-dimensional images, such as A-scan, two-dimensional images, such as a B-scan, and/or three-dimensional images. Once the polar coordinates of the object are detected, the polar coordinates can be converted to the Cartesian coordinates and displayed as a tomographic image. Thus, a three-dimensional profile of the stent can be detected and displayed to a user. In addition, with the polar coordinates of the stent automatically detected, the strent stut apposition or coverage relative to the lumen border can easily be computed. Additionally, these algorithms can be applied to pre-scan converted data and to scan converted data.

Because the algorithms disclosed herein can be applied to every frame taken during an OCT imaging run, the location of the object can be detected in one or more frames can be computed and provided to the user on a graphic display.

The 1-D, 2-D or 3-D images include data, such as pixel data, which includes pixel locations, pixel intensity, color intensities, which includes the RGB color channel for the pixels, and/or volumetric data, which includes the x, y, z coordinates. The data obtained from the image are considered features within the image that can be used to classify or detect the object. Images can be associated with other data features such as amplitude, phase, frequency, polarity, velocity, weight, density, transparency, reflectance, hardness, and temperature.

Figure 14:
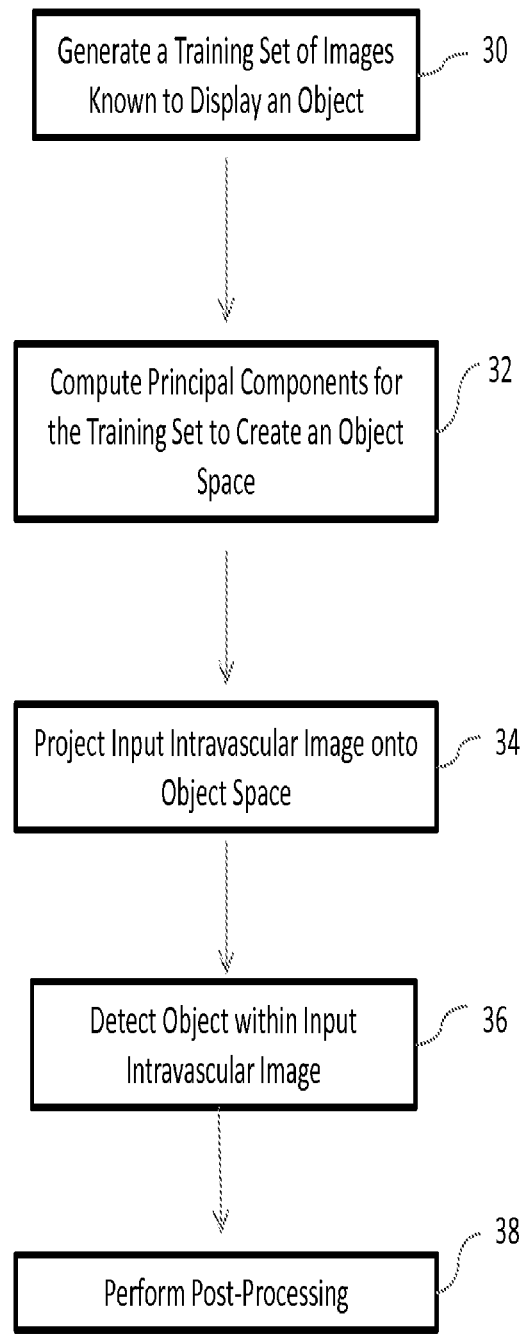
FIG. 14 depicts a basic flow chart for principal component analysis for stent detection.

FIG. 14 exemplifies the steps employed in an embodiment for detecting stents using an adaptation of principal component analysis, a known signal processing approach. Exemplary principal components analysis techniques can be found in M. Turk and A. Pentland "Eigenfaces for Recognition" and Pentland et al. "View-based and modular eigenspaces for face recognition" in Proc. IEEE Conf. Comput Vision. @ Pattern Recogn. These techniques have been adapted to of detection of object in intraluminal images. The first step 30 includes generating a training set of pre-defined intraluminal images for an object. The second step 32 involves computing the principal components for the object to create an object space. The third step 34 involves projecting an input intraluminal image onto the object space. The fourth step 36 involves detecting the object within the intraluminal image. Methods of the invention are not limited to stent detection, but can be used to detect any object within an intraluminal image, such as guidewire, lumen border, and tissue.

The first step 30 is to generate a training set of pre-defined intraluminal images known to contain an object so that the images can be used to train the processor to identify the object within images or regions of images not known to contain the object. Images known to contain the object include images in which the object was manually located and detected. The images known to contain the object can be obtained online or compiled off-line. In certain aspects, the training set of pre-defined intraluminal images can be pre-processed by, for example filtering the images prior to generating a training set.

In certain aspects, the images for the training set are all the same size or interpolated to the same size. Data, such as pixel intensity, can be arranged into a matrix for principal component analysis. In one aspect, data from each image in the training set can be taken and stacked into a matrix, wherein each column in the matrix represents a different image and each row within a column of the matrix represents the same pixel location in each training image. The rows can be through of as features and each column is a sample of that feature.

It should be noted that in all training sets generated for use in the embodiments described herein are not limited to a fixed amount of pre-defined images. Rather, the training sets can be made to have an adaptive training process. For example, by continually updating training sets with input intraluminal images that have been positively identified for a specific object. As the training set database grows, so does the accuracy of the detection.

Once a matrix for the training set of pre-defined matrix is compiled, the principal components for the training set matrix are computed to create an object space, as in the second step 32. The principal components can be computed by directly computing the eigenvectors of a covariance matrix computed from the training data set matrix or by utilizing Singular Value Decomposition (SVD) of the training set data matrix, which is described in detail in, for example, Abdi, H, & Williams, L. J. (2010). "Principal component analysis." *Wiley Interdisciplinary Reviews: Computational Statistics,* 2: 433-459. By calculating the principal components, one can determine which vectors out of the set of pre-defined images best account for the distribution of object images within the entire object space. Therefore, only the top n eigenvectors are kept in order to create a basis which accounts for most of the variance within the image set. These vectors define the subspace of object images, and constitute the object space. The principal components are stored within a memory and utilized later on to detect an object within input intraluminal images.

In order to utilize the principal components to detect object in unknown input images, a threshold error can be computed. In one aspect, the threshold value is computed by determining the amount of error between one or more of pre-defined images known to contain the object and the object space. This threshold error can be obtained using the same pre-defined images that were used to create the object space or another image known to create the same object. In order to determine error, a pre-defined image can be projected onto the object space in order to determine the distance between points in the pre-defined image in comparison to the object space. In certain aspects, the error is the Euclidean distance between the training set image and the object space. This error computation can be repeated for each pre-defined image in the training set, a portion of pre-defined images in the training set, or for multiple pre-defined images outside of the training set.

Using the computed errors, one can calculate a threshold error value that can be used to determine if an unknown image contains the object. For example, unknown images that are projected against the object space that have an error greater than the threshold error will not be determined to contain the object and unknown images with an error smaller than the threshold error will return a positive detection for the object. The threshold error can be the maximum error, minimum error, or an average computation of the error, such as the quadratic mean, arithmetic mean, mode, medium, or any other statistical average known in the art.

The third step 34 involves projecting an input intraluminal image onto the object space. The input intraluminal image can be an image taken during an OCT procedure in real-time or a previously taken image, for example, an image that was stored or uploaded onto the computing system. The error between the input intraluminal image and the object space is computed in a similar manner the error was computed for each pre-defined image to determine a threshold error. In some embodiments, the error is the Euclidean distance between the input image and the object space. After the error is computed, the error of the input intraluminal image can be used to detect the object, as in the fourth step 36. For example, if the error is below a threshold value, the object is positively detected in the input intraluminal image. If the error is above the threshold image, then the object is negatively detected within input intraluminal image.

In certain aspects, an object space is created for two or more objects in order to compare the input intraluminal image to two or more object spaces. Step 30 and step 32 are repeated for at least one other object. In one embodiment, a training set is generated of pre-defined intraluminal images known to contain stents and a training set is generated of pre-defined intraluminal images known to contain tissue, for example, imaging of a blood vessel without stents. The principal components are generated for both training sets to compute a tissue space and a stent space. For step 36, an input intraluminal image can be projected onto both the tissue space and the stent space, and a tissue error and a stent error can be calculated by comparing the input intraluminal image to both spaces. The set of principal components, tissue or stent, which most accurately represents the original image, is selected as the class matching the input intraluminal image, and the corresponding object is positively detected. For example, if the error between the stent and the input intraluminal image is less than the error between the tissue and the input intraluminal image, the stent is positively detected within the input intraluminal image.

In addition, a threshold error value can also be computed for each of the plurality of object spaces. A comparison between the input intraluminal image and each object space's threshold value can determine whether or not the object is present in the input intraluminal image. If the error is significantly high for both classes, this can indicate that the input intraluminal image does not match any of the data that was used in the training set. Comparing threshold error reduces the risk of misclassification when comparing simply comparing the magnitudes of the error. If the input intraluminal image does not match any of the training sets, an indicator can appear on an OCT graphical display to indicate to the user that manual detection may be required with respect to the unclassified input intraluminal image.

In a specific embodiment, method of FIG. 14 is adapted to train the classifier to detect tissue, stents, and guidewires. Guidewires are often misclassified as a stent strut because its features appear stent like in the intraluminal images. This prevents the likelihood that a positive detection for a stent is actually a guidewire.

In some embodiments, the input intraluminal image may be defined using the lumen border. In order to improve performance, the detected lumen border can be used to identify search regions for the object, such as a stent strut, within the image. In this aspect, the training sets of pre-defined images generated for an object will also be defined by the lumen border. For example, if a lumen border is detected within a region around +30 pixels, −200 pixels within an A-line, a training set can be formed using only the lumen border region of pre-defined images and an object space for that region can be generated. The same region of the A-line intraluminal image can be projected onto the object space to detect the object in that region. Detection occurs using the same error methods as previously described. The lumen border can be automatically or semi-automatically detected in an image using any method known in the art, such as the techniques disclosed in U.S. Pat. No. 7,978,916, S. Tanimoto, G. Rodriguez-Granillo, P. Barlis, S. de Winter, N. Bruining, R. Hamers, M. Knappen, S. Verheye, P. W. Serruys, and E. Regar, "A novel approach for quantitative analysis of intracoronary optical coherencetomography: High inter-observer agreement with computer-assisted contour detection," Cathet. Cardiovasc. Intervent. 72, 228-235 (2008); K. Sihan, C. Botka, F. Post, S. de Winter, E. Regar, R. Hamers, and N. Bruining, "A novel approach to quantitative analysis of intraluminal optical coherence tomography imaging," Comput. Cardiol. 1089-1092 (2008); J. Canny, "A computational approach to edge detection," IEEE Trans. Pattern Anal. Mach. Intell. 8, 679-698 (1986).

Additionally, methods of the invention provide for a post-processing step to, for example, detect the location of the stent within the image, for example, the stent depth. Any method known in the art can be used to locate the depth position of the stent, such as peak detection within some maximum distance of the detected lumen border can be used to identify the final location of the stent. Post-processing can be used to verify the detection of the stent within the image. For example, methods of the invention can also be combined with other algorithms or methods used to detect guidewires or other false stent detections. In one aspect, after detection of stents using the methods of the invention, a guidewire detection/tracking algorithm can be applied to the image to remove the false stent detections. Post-processing can also be used to visually illustrate the resulting stent detections within the intravascular image on a graphical user interface. For example, detected portions of the stent can be highlighted with a bolded line or circled within the image.

Figure 15:
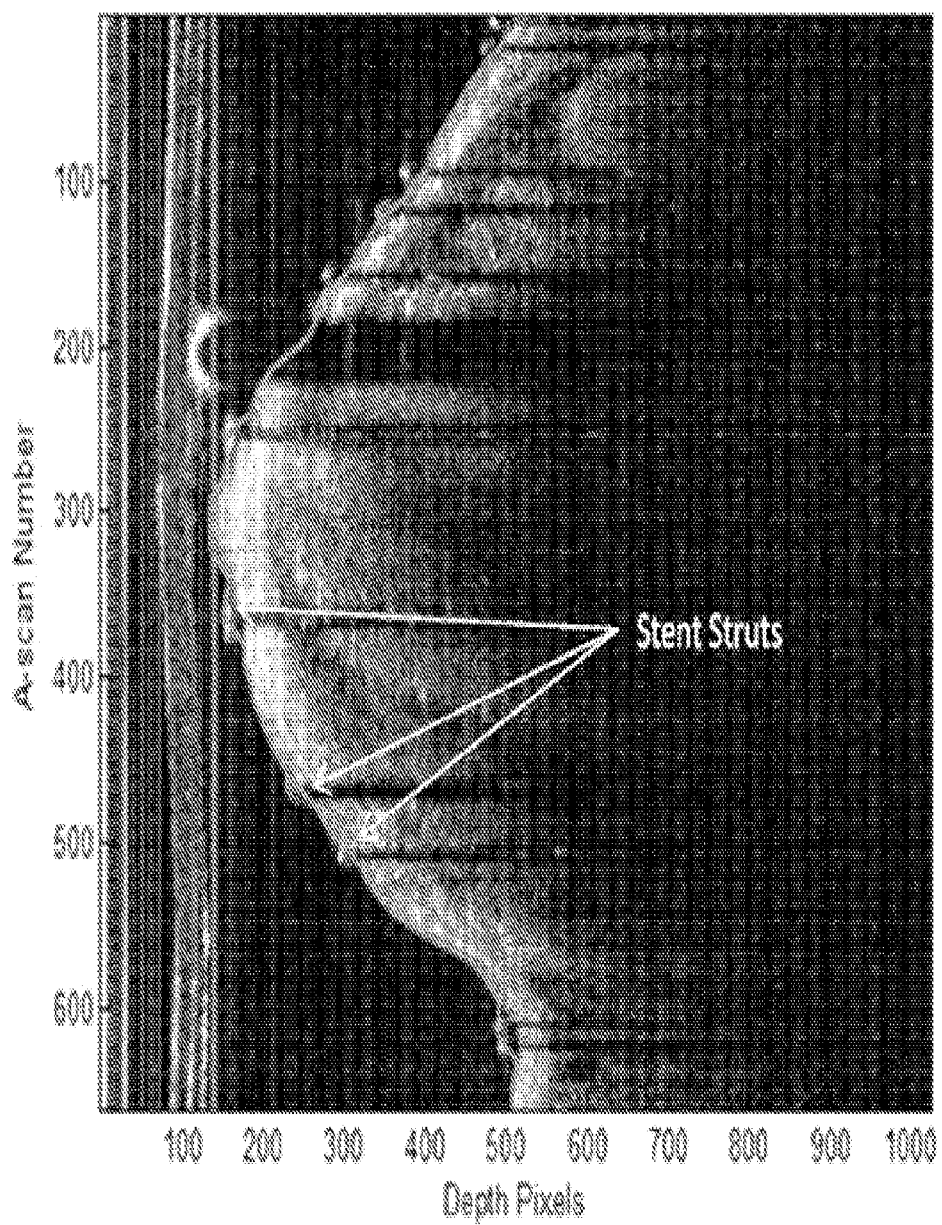
FIG. 15 depicts an example OCT B-Scan with stent struts detected following the principal component analysis outlined in FIG. 14.
Figure 16:
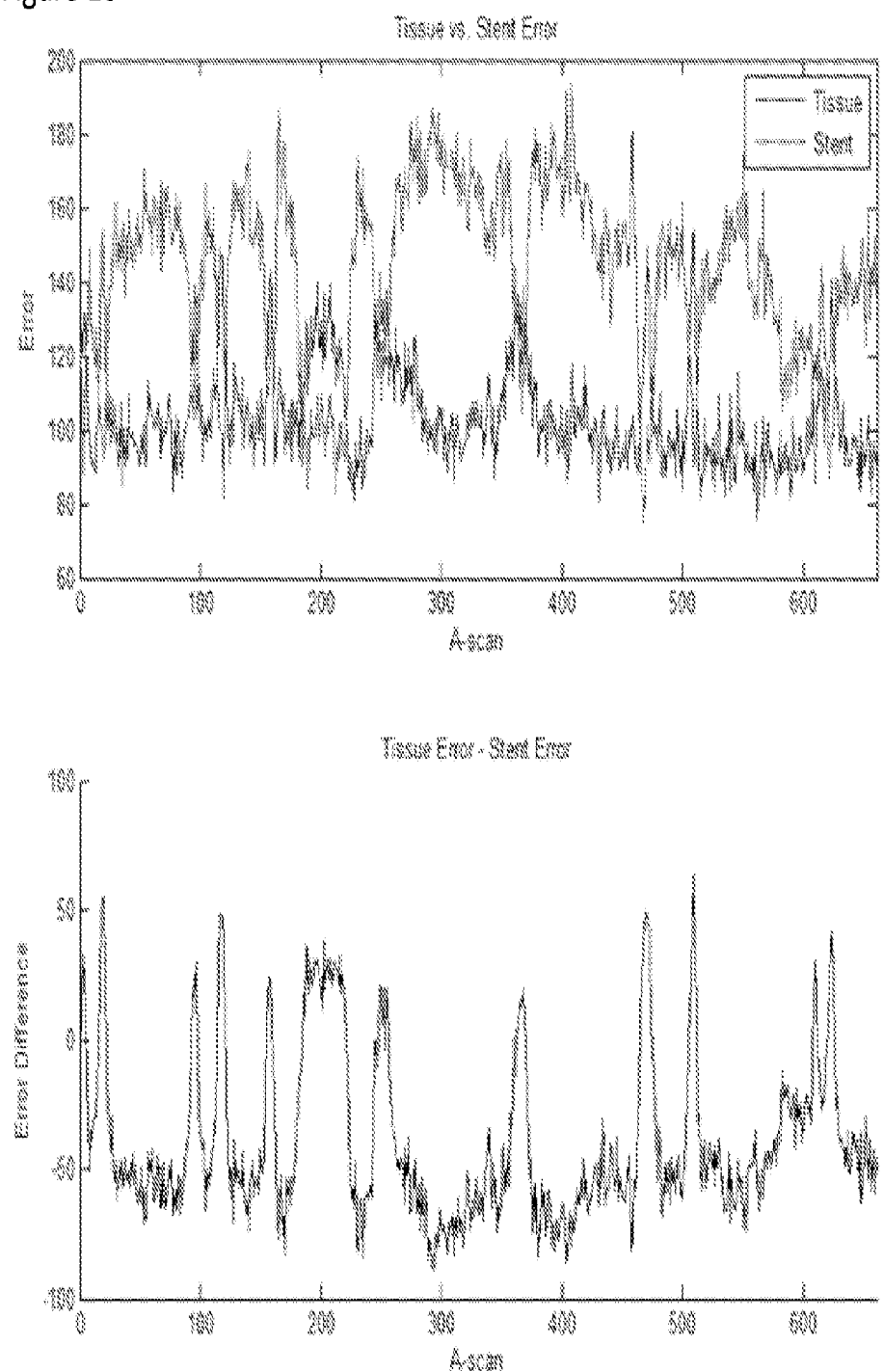
FIG. 16 depicts the error of projected data using stent and tissue principal components.
Figure 17:
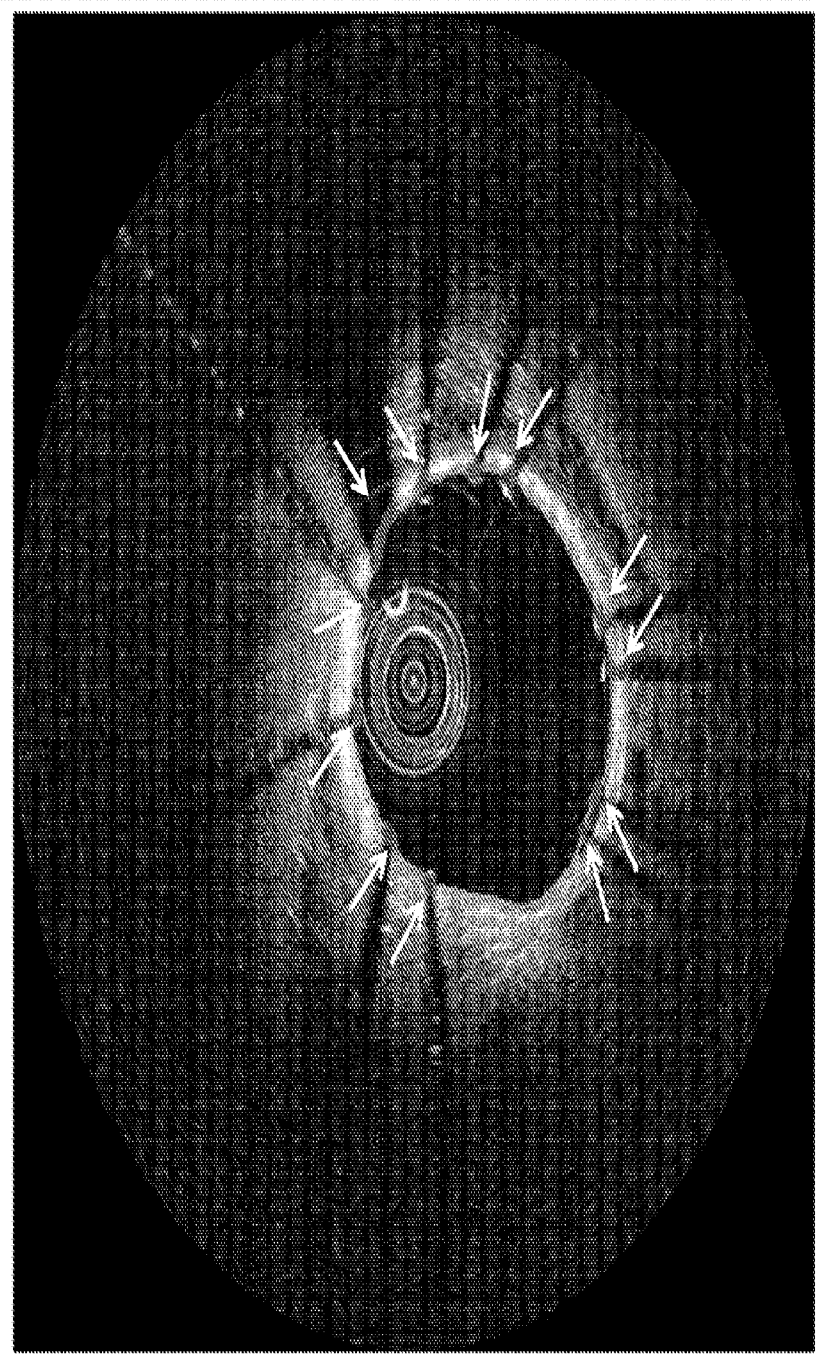
FIG. 17 depicts the resulting stent detections in scan-converted image of FIG. 15.
Figure 18:
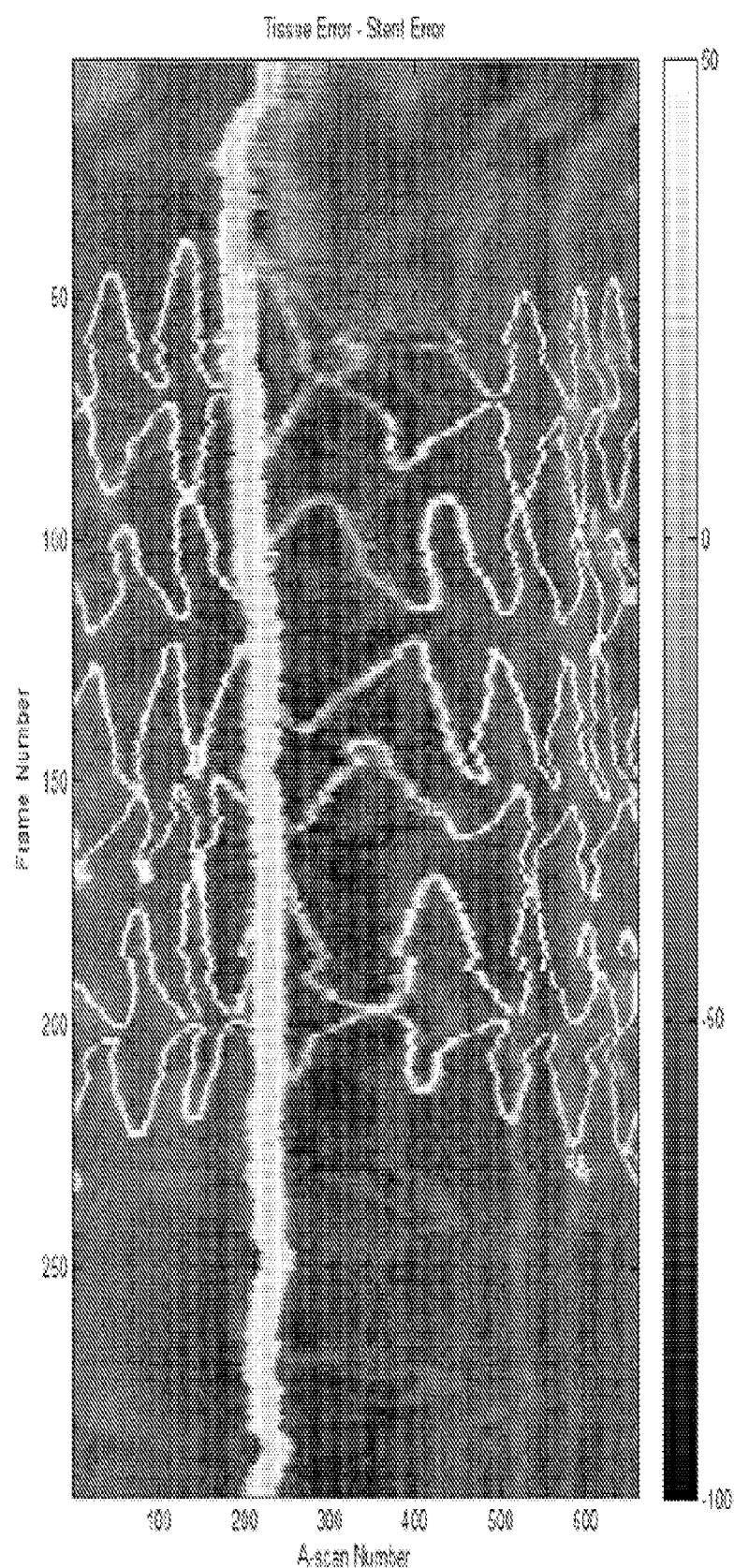
FIG. 18 depicts the tissue error and stent error from FIG. 16 for all frames in a pullback.
Figure 19:
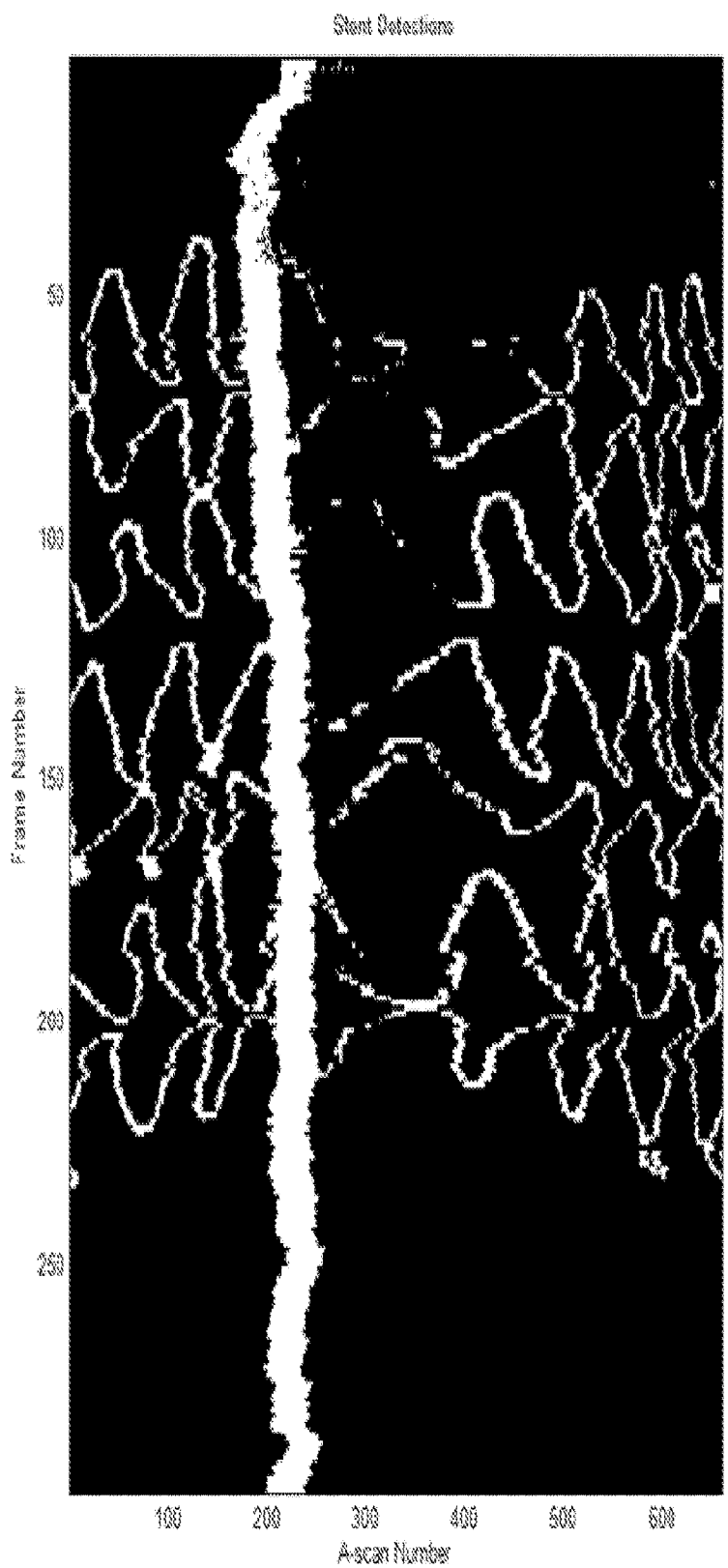
FIG. 19 depicts the corresponding stent detections from for all frames in a pullback.

The following description and figures illustrate stent detection following the block diagram in FIG. 14. FIG. 15 depicts an example of an OCT B-scan highlighting both detected stent struts and the automatically detected lumen border. A training set for stents and tissue were generated defined by the lumen border and a tissue space and stent space were computed. The A-line input intraluminal image around the border was projected onto a stent space and a tissue space. The error between the input intraluminal image and both the tissue space and stent space were computed, and plotted in FIG. 16. As shown in FIG. 16, the stent error is smaller at the location of the stents and the tissue error is higher at the locations of the stents. The difference between the stent error and the tissue error is also plotted in FIG. 16. Locations along the lumen border where the stent error is lower than the tissue error are classified as stents, and thus a stent is positively detected within the image. FIG. 17 displays the corresponding scan-converted image of the B-scan shown in FIG. 15. Post-processing was utilized to highlight the stent detections within the scan-converted image. The difference between the stent and tissue error for all frames in a pullback is plotted in a 2D splayed map in FIG. 18. The corresponding stent detections for all frames in this pull-back are provided in FIG. 19.

In another embodiment, objects are detected within an intraluminal image using region covariance descriptors to detect objects in images or in regions of images. This approach can be adapted to both 1D, 2D, and 3D intraluminal images. Similar to the detection method outlined in FIG. 13, this algorithm requires generating a training step of pre-defined intraluminal images and determining a compute for the training set that is compared to an input intraluminal image for detection. Regional covariance imaging techniques are known in the art and are described in, for example, Tuzel et al. "Region Covariance: A Fast Descriptor for Detection and Classification," European Conference on Computer Vision (ECCV), May 2006; Forstner and Moonen, "A metric for covariance matrices," Technical Report, Dept. of Geodesy and Geoinformatics, Stuttgart University (1999).

To detect stents or objects within intraluminal images using regional covariance, the first step is to generate a training set of pre-defined intraluminal images known to contain an object, for example, stent, tissue, or guidewire. A feature matrix can then be generated for the training set using a number of features within each pre-defined intraluminal image of the training set, e.g., the x and y coordinates of the pixel location, intensity of each pixel, and the first and second order derivatives of the image in the x and y direction. These features are computes for each pre-defined image within the training set. A pre-defined image of the training set can be any size image of m×n, and in one aspect m and n correspond to a dimension that is slightly larger than the width of a stent and the depth of tissue in an intraluminal image, and all images of the training set should be the same size. Although it is possible to perform regional covariance analysis on the entire image, use of m×n regions allows for targeted search of stents and other objects located on the lumen border. For example, the m×n image region can be created around the lumen border detected within an input intraluminal image, using any method of detecting the lumen border known in the art and discussed above.

Each pixel of a pre-defined intraluminal image is converted in to a feature matrix, using the equation listed below.

Feature Matrix for Region Covariance Tracking [1]

Equation 1

$$F(x, y) = \left[ \begin{bmatrix} x & y & I(x, y) & \left|\frac{\partial I(x, y)}{\partial x}\right| & \left|\frac{\partial I(x, y)}{\partial y}\right| & \left|\frac{\partial^2 I(x, y)}{\partial x^2}\right| & \left|\frac{\partial^2 I(x, y)}{\partial y^2}\right| \end{bmatrix} \right]$$

In the above equation, x and y are indices and I is the intensity. For purposes of stent detection, the feature equation can be adapted to have more or less features or contain additional feature data, for example, the addition of RGB color values. Each input intraluminal image within the training set will have the same (x, y) pixel locations, and although not distinguishing, these coordinates are useful to correlate other features that vary from image to image. Once the feature matrix is computed, a covariance matrix for the set of features for each image can be computed using the following equation, where z represents the features, u is the mean of the feature samples, and T is a transpose operator.

$$C_R = \frac{1}{n-1} \sum_{k=1}^{n} (z_k - \mu)(z_k - \mu)^T \qquad \text{Equation 2}$$

The above process is repeated for each pre-defined intraluminal image within the training set, and the covariance matrices are saved in the memory for later use during detection of objects of unknown input intraluminal images. The covariance matrices represent subspaces of the object.

In order to detect an object in the input intraluminal image, the input intraluminal image is broken down into the same m×n regions as the pre-defined images of the training set to identify, for example, stent locations. The covariance matrix of the input intraluminal image for the region is computed and compared to each covariance matrix of the training set. The comparison of the covariance matrix involves performing a distance calculation, or error calculation, between feature points within the covariance matrices. Any method known in the art for calculating the distance between covariance matrices can be used or adapted to calculate the distance between the unknown input intraluminal image covariance matrix and the covariance matrices of the pre-defined training. See for example, J. N. L. Brümmer and L. R. Strydom, "An euclidean distance measure between covariance matrices of speechcepstra for text-independent speaker recognition," in Proc. 1997 South African Symp. Communications and Signal Processing, 1997, pp. 167-172; W. Forstner and B. Moonen, A Metric for Covariance Matrices Dept. Geodesy and Geoinformatics, Stuttgart Univ., Stuttgart, Germany, 1999; Ö Tüzel, F. Porikli, and P. Meer, "Region covariance: A fast descriptor and for detection and classification," in Proc. Image and Vision Computing, Auckland, New Zealand, 2004.

A threshold error can be determined for the training set and used to determine whether the distance between the input intraluminal image and training set images are indicative of a positive detection of the object. Any method can be used to create a threshold distance. For example, the threshold distance is obtained by calculating the covariance distance between the training set images and selecting the maximum distance as a threshold distance, or calculating an average value as a threshold distance.

Like previous embodiments, the regional covariance approach can also be used to detect one or more objects within an input intravascular image by generating covariance matrices for more than one object. For example, a training set of pre-defined images can be generated for tissue and stents, features matrices can be computed for each pre-defined image within a training set, and a covariance matrix can be calculated from each feature matrix. A covariance matrix calculated for an input intraluminal image is then compared to the stent and tissue covariance matrices. The training set that minimizes the distance from input intraluminal image indicates a positive detection of the object corresponding to the training set within the input intraluminal image. In addition, a threshold error can be computed for each object, and used to determine if the either object is present in the intravascular image.

Figure 20:
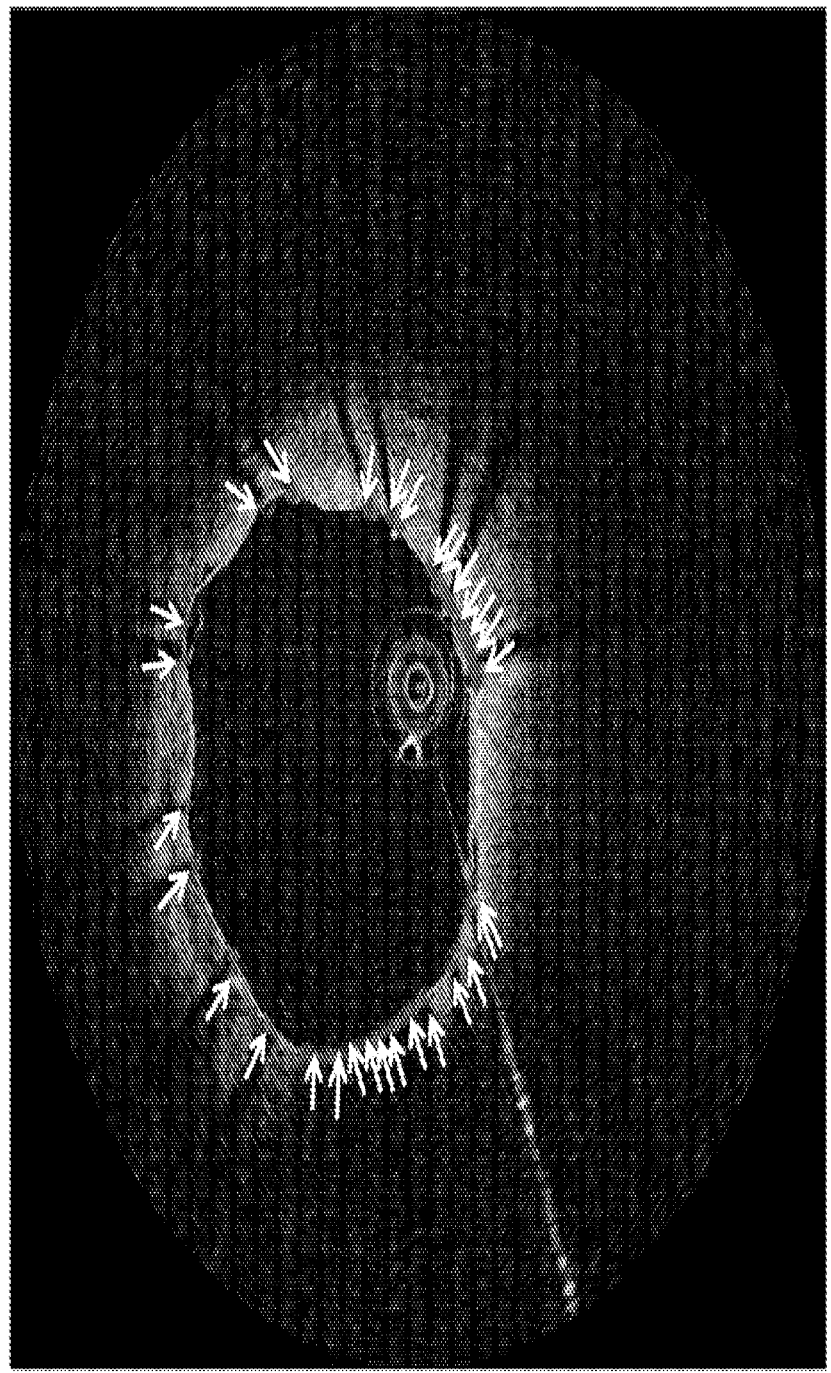
FIG. 20 depicts the resulting stent detections using regional covariance analysis.

FIG. 20 displays detected stent struts within A-scan-converted image using the regional covariance approach. The bolded lines indicate the stent detections. Like the previously discussed embodiments, post-processing can be applied to identify the location of the stent in depth and remove false detections.

In addition, other algorithm image processing techniques known in the art that utilize subspaces for object recognition within images can adapted to detect stents and other objects in intraluminal images. For a concise overview of various object recognition techniques, see Bain and Tao, Chapter 3: "Face Subspace Learning", Handbook of Face Recognition, 2011. For example, Fisher's linear discriminate analysis (FLDA) can be used to detect stents. Linear discriminant analysis is primarily used to reduce the number of features, such as pixel values, to a more manageable number before classification or detection as compared to using principal component analysis. Each of the new dimensions is a linear combination of pixel values, which form a template. The linear combinations obtained using Fisher's linear discriminant is called a linear classifier and can be used in comparison to input intraluminal images to detect stents.

In certain aspects, FDLA can be combined with other algorithmic techniques to improve the accuracy of object detection using the technique. For example, FDLA can be combined with general mean criterion and max-min distance analysis (MMDA), discriminatory locality alignment analysis (DLA), and manifold elastic net (MNE).

Another detection method that can be used or adapted to detect stents or objects in intraluminal images includes using statistical model-based image recognition algorithms. See, for example, Felzenszwalb and Huttenlocher, "Pictorial Structures for Object Recognition," Volume 61, Number 1, 55-79, DOI: 10.1023/B:VISI.0000042934.15159.49; A. A. Amini, T. E. Weymouth, and R. C. Jain. "Using dynamic programming for solving variational problems in vision," IEEE Transactions on Pattern Analysis and Machine Intelligence, 12(9):8551867, September 1990; M. A. Fischler and R. A. Elschlager, "The representation and matching of pictorial structures," IEEE Transactions on Computer, 22(1): 67-92, January 1973.

With respect to the methods of detecting objects within intraluminal images discussed herein, various computer or processor-based systems are suitable for compiling data from intraluminal images, interfacing with an OCT probe to obtain input intraluminal images, applying the disclosed algorithms to detect objects, and displaying the detected objects to a user of the OCT system. The systems and methods of use described herein may take the form of an entirely hardware embodiment, an entirely software embodiment, or an embodiment combining software and hardware aspects. The systems and methods of use described herein can be performed using any type of computing device, such as a computer, that includes a processor or any combination of computing devices where each device performs at least part of the process or method.

In some embodiments, a device of the invention includes an OCT imaging system and obtains a three-dimensional data set through the operation of OCT imaging hardware. In some embodiments, a device of the invention is a computer device such as a laptop, desktop, or tablet computer, and obtains a three-dimensional data set by retrieving it from a tangible storage medium, such as a disk drive on a server using a network or as an email attachment.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Figure 21:
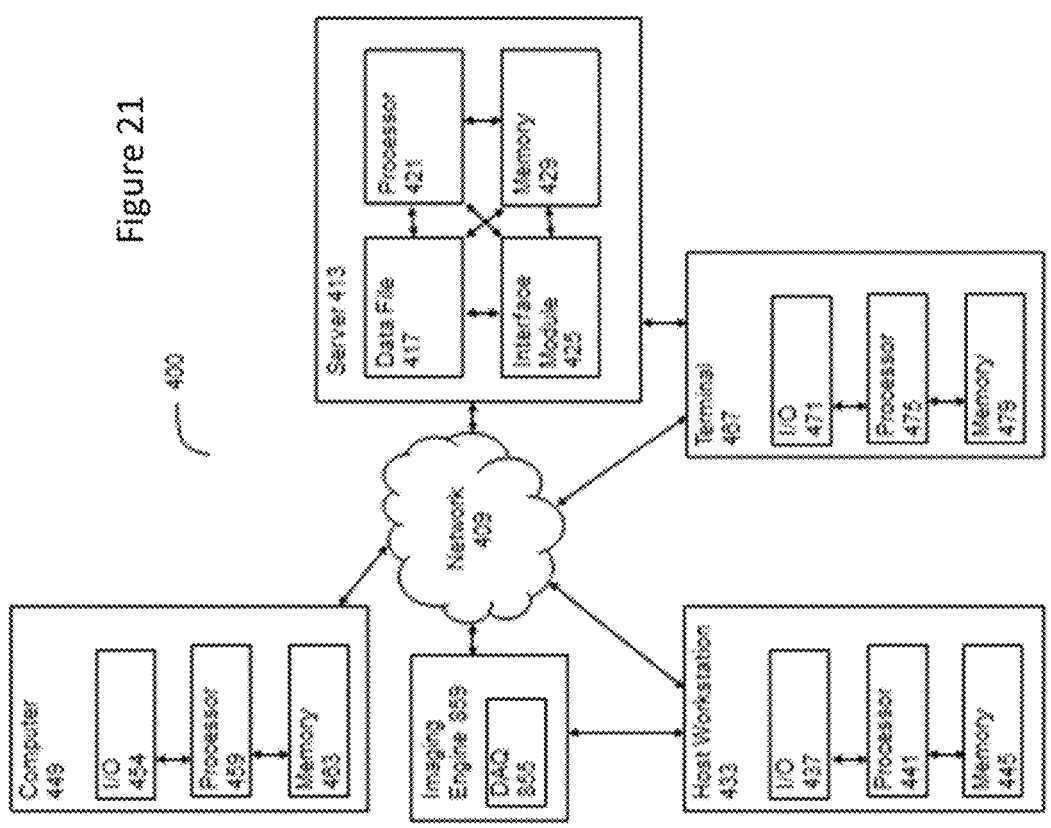
FIG. 21 is a system diagram according to certain embodiments.

In some embodiments, a user interacts with a visual interface to view images from the imaging system. Input from a user (e.g., parameters or a selection) are received by a processor in an electronic device. The selection can be rendered into a visible display. An exemplary system including an electronic device is illustrated in FIG. 21. As shown in FIG. 21, imaging engine 859 communicates with host workstation 433 as well as optionally server 413 over network 409. In some embodiments, an operator uses computer 449 or terminal 467 to control system 400 or to receive images. An image may be displayed using an I/O 454, 437, or 471, which may include a monitor. Any I/O may include a keyboard, mouse or touchscreen to communicate with any of processor 421, 459, 441, or 475, for example, to cause data to be stored in any tangible, nontransitory memory 463, 445, 479, or 429. Server 413 generally includes an interface module 425 to effectuate communication over network 409 or write data to data file 417.

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server 413), a middleware component (e.g., an application server), or a front-end component (e.g., a client computer 449 having a graphical user interface 454 or a web browser through which a user can interact with an implementation of the subject matter described herein), or any combination of such back-end, middleware, and front-end components. The components of the system can be interconnected through network 409 by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a portion of file 417 that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over network 409 (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

It will be understood that each block of the FIG. 14, as well as any portion of the systems and methods disclosed herein, can be implemented by computer program instructions. These program instructions may be provided to a processor to produce a machine, such that the instructions, which execute on the processor, create means for implementing the actions specified in the FIG. 14 or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A computer-readable, non-transitory medium storing software code representing instructions that when executed by a computing system cause the computing system to perform a method of detecting an object within an image, the method comprising:
    obtaining pre-defined data associated with the object disposed in a body lumen;
    computing principal components for the pre-defined data to create an object space for the object disposed in a body lumen, wherein the computing comprises determining a threshold error using the pre-defined data and the object space;
    projecting an input image onto the object space, wherein the projecting comprises determining an input image error by a second comparison of the input image and the object space; and
    detecting the object disposed in the body lumen in the input image based on the input image error and the threshold error.

2. The computer-readable, non-transitory medium of claim 1, wherein an input image error less than the threshold error constitutes a positive detection of the object disposed in the body lumen in the input image.

3. The computer-readable, non-transitory medium of claim 1, wherein the pre-defined images and input image are one-dimensional, two-dimensional, or three-dimensional.

4. The computer-readable, non-transitory medium of claim 1, further comprising post-processing the input image.

5. The computer-readable, non-transitory medium of claim 4, wherein the step of post-processing comprises removing false detections and highlighting detections of objects disposed in the body lumen.

6. The computer-readable, non-transitory medium of claim 1, further comprising
    performing the steps of generating, identifying, and projecting for at least one other object; and
    detecting the at least one other object in the input image.

7. The computer-readable, non-transitory medium of claim 6, wherein the step of detecting the at least one other object further comprises
    calculating an error between the input image and the object space for the object disposed in the body lumen and between the input image and the object space for the at least one other object.

8. The computer-readable, non-transitory medium of claim 7, further wherein a small error constitutes a positive detection for the corresponding object.

9. The computer-readable, non-transitory medium of claim 6, wherein the pre-defined images and input image are one-dimensional, two-dimensional, or three-dimensional.

10. The computer-readable, non-transitory medium of claim 1, wherein the body lumen is a vasculature lumen.

11. The computer-readable, non-transitory medium of claim 1, wherein the object disposed in the body lumen is selected from the group consisting of a stent, a stent strut, a guidewire, and tissue.

12. A system for automatically detecting an object within an image, comprising:
- a central processing unit (CPU); and
- a storage device coupled to the CPU and having stored there information for configuring the CPU to:
  - obtain pre-defined data associated with an object disposed in the body lumen;
  - compute principal components for the pre-defined data to create an object space for the object disposed in the body lumen, wherein the computing comprises determining a threshold error using the pre-defined data and the object space; and
  - project an input data image onto the object space, wherein the projecting comprises determining an input image error by a second comparison of the input image and the object space;
  - detect the object disposed in the body lumen in the input image based on the input image error and the threshold error.

13. The system of claim 12, wherein an input image error less than the threshold error constitutes a positive detection of the object disposed in the body lumen in the input image.

14. The system of claim 12, wherein the pre-defined images and input image are one-dimensional, two-dimensional, or three-dimensional.

15. The system of claim 12, further comprising post-processing the input image.

16. The system of claim 15, wherein post-processing comprises removing false detections and highlighting detections of objects disposed in the body lumen.

17. A method for detecting an object in an intraluminal image, the method comprising the steps of:
- obtaining pre-defined data associated with an object disposed in the body lumen;
- computing principal components for the pre-defined data to create an object space for the object disposed in the body lumen, wherein the computing comprises determining a threshold error using the pre-defined data and the object space;
- projecting an input image onto the object space, wherein the projecting comprises determining an input image error by a second comparison of the input image and the object space; and
- detecting the object disposed in the body lumen in the input image based on the input image error and the threshold error.

18. The method of claim 17, further comprising processing the input image.

19. The method of claim 18, wherein said processing step processing comprises removing false detections and highlighting detections of objects disposed in the body lumen.

* * * * *